United States Patent [19]

Lechevin et al.

[11] 4,241,047

[45] Dec. 23, 1980

[54] NOVEL MEDICINAL COMPOSITION FOR THE TREATMENT OF BILIARY LITHIASIS

[75] Inventors: Jean-Claude Lechevin, Lyons; Jean-Noël Treilles, Lissieu-Lozanne, both of France

[73] Assignee: Lipha, Lyonnaise Industrielle Pharmaceutique, Lyons, France

[21] Appl. No.: 815,424

[22] Filed: Jul. 18, 1979

[51] Int. Cl.³ ............... A01N 45/02; A61K 31/575; A61K 9/32; A61K 9/40
[52] U.S. Cl. .................... 424/33; 424/238; 424/35; 424/37; 260/397.1; 424/240
[58] Field of Search ............ 424/238, 240, 3, 33, 424/35, 37; 260/397.2, 397.1

[56] References Cited

U.S. PATENT DOCUMENTS

| 3,175,943 | 3/1965 | Molho et al. | 424/238 |
| 4,079,133 | 3/1978 | Drees et al. | 424/238 |

OTHER PUBLICATIONS

*Northfield et al.,* "Gut", (1975), vol. 16, pp. 1–17.
*Danzinger et al.,* "New Eng. Jour. Med.", (1972), 286, pp. 1–8.
Therapie (1968) (XXIII), article by Fontaine et al., pp. 52–62.
P. Vayre et al., J. Med. Cher. Dig. (1974), No. 3, pp. 293–297.

*Primary Examiner*—Elbert L. Roberts
*Attorney, Agent, or Firm*—Browdy and Neimark

[57] ABSTRACT

The invention concerns a novel medicinal composition for the treatment of biliary lithiasis. The active principle of the composition is formed by the association of hymecromone (4-methyl-7-hydroxycoumarine) and chenodeoxycholic acid. The medicament is administered by oral route in a suitable pharmaceutical form.

9 Claims, No Drawings

NOVEL MEDICINAL COMPOSITION FOR THE TREATMENT OF BILIARY LITHIASIS

The present invention concerns a novel medicinal composition for the treatment of biliary lithiasis.

It is known that biliary lithiasis is characterised by the presence in the bile of calculi formed essentially of cholesterol. Under normal physiological conditions, the water-insoluble cholesterol is solubilized in the bile in the form of a colloidal solution, thanks to the phospholipids and particularly to the biliary salts which permit the formation of micellae. Under pathological conditions, with subjects suffering from lithiasis, the cholesterol-enriched bile is incapable of completely solubilizing the cholesterol. The cholesterol excess precipitates and forms the vesicular calculi.

It is known from the work carried out by Danzinger and collaborators (N. Engl. J. Med. 1972, 286, 1-8) that chenodeoxycholic acid ($C_{24}H_{40}O_4$, molecular weight 392.56) is capable of dissolving the vescular calculi when administered by oral route. These results have since been confirmed by numerous references.

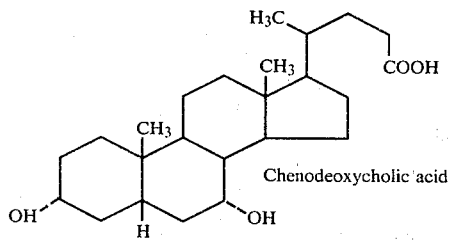

Chenodeoxycholic acid

It is also known from work carried out by NORTHFIELD and collaborators (Gut. 1975, 16, 1-17) that chenodeoxycholic acid acts essentially by decreasing the biliary secretion of the cholesterol.

This effect could result from a diminution of the hepatic synthesis of the cholesterol (Salen and collaborators, Clin. Res., 1973, 21, 523).

The use of chenodeoxycholic acid for the treatment of biliary lithiasis thus is of a certain degree of interest, but it is not without harmful secondary effects. In particular, there is noted a poor digestive tolerance with fairly frequent attacks of diarrhea, which are sometimes considerable and not well tolerated, a certain hepatic intolerance, with a raising of the transaminases and of the γ-glutamyl transpeptidase. Moreover, the treatment is costly, because of the cost of the product and the amount of the posology.

According to the present invention, there has been found a means of overcoming the aforementioned inconveniences, secondary effects and cost of the treatment, by associating with the chenodeoxycholic acid a compound which is a spasmolytic of the main biliary duct and of the sphincter of Oddi and is choleretic: hymecromone ($C_{10}H_8O_3$—molecular weight 176, 173).

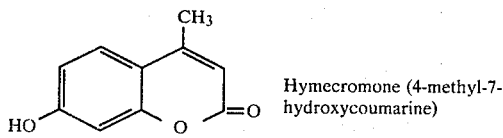

Hymecromone (4-methyl-7-hydroxycoumarine)

Hymecromone, a spasmolytic of the main biliary duct and of the sphincter of Oddi (VAYRE and HUREAU, Med. Cher. Dig. 1974, 3, 293-297) enlarges the diameter of the choledochus, opens the sphincter of Oddi and as a result facilitates the evacuation of the small size biliary calculi in the duodenum.

The choleretic hymechromone (FONTAINE L. and collaborators, Therapie, 1968, 23, 51-62, and U.S. Pat. No. 3,175,943), by increasing the volume of discharged bile, assures the flushing of the biliary duct and renews the contact of the calculi with the bile, and consequently causes a more rapid dissolving of the vesicular calculi.

Moreover, hymecromone is capable of modifying the composition of the bile, by decreasing particularly the concentration of cholesterol, as indicated in the following table, which gives the average of the results obtained in connection with five dogs after oral administration of hymecromone in the dose of 25 mg per kg.

|  | Cholesterol content in the bile (mg/liter) |
| --- | --- |
| Before treatment | 420 |
| 30 minutes after treatment | 102 |
| 1 hour after | 110 |
| 1½ hours after | 132 |
| 2 hours after | 145 |
| 2½ hours after | 170 |

The similar properties of chenodeoxycholic acid and hymecromone (decrease in the concentration of cholesterol in the bile) and the complementary properties of the hymecromone (spasmolytic and choleretic properties) make it possible, according to the present invention, to improve the effects of the chenodeoxycholic acid during lithiasis. Furthermore, hymecromone has an excellent digestive tolerance. The result of the association is in fact an improvement in the tolerance, a reduction in the cost of treatment and an improvement in the rapidity of the effects.

Moreover, the spasmolytic and choleretic properties of the hymecromone permit an eventual elimination of the small calculi in the duodenum, and as a result avoiding an occlusion of the choledochus by the small size calculi which would have migrated after partial dissolution.

Consequently, the therapeutic properties of hymecromone either permit the posology of the chenodeoxycholic acid to be decreased, thereby causing an attenuation of the secondary effects due to the chenodeoxycholic acid and a reduction in the cost of treatment, or a shortening of the treatment time.

The association in accordance with the invention comprises hymecromone in an amount varying from 100 to 500 mg per dose and chenodeoxycholic acid in an amount varying from 20 to 300 mg per dose. The daily posologies may be from 300 to 2400 mg per day for hymecromone and from 100 to 1000 mg per day for chenodeoxycholic acid. This association is administered orally in any one of the pharmaceutical forms conventionally used for this purpose (tablets, coated tablets, hard gelatine capsules, soft gelatine capsules, solutions, suspensions . . . ). The tablets may contain the association of the active principle and an excipient formed of gelatine, algic acid, talcum and magnesium stearate. The tablets may be covered with a sugar coating. The coated tablets are covered with a polymer-based film: for example, derivatives of cellulose, derivatives of acrylic acid. The hard gelatine capsules contain a powder of the active principle and the excipient, such as magnesium stearate. The soft gelatine tablets contain a suspension of the active principle in polyoxyethylene glycol. The suspensions to be taken orally contain the active principle, in suspension in purified water containing a preservative.

A few examples of pharmaceutical forms which illustrate the invention are given below, without any limiting character.

EXAMPLES

EXAMPLE 1

Tablet containing 300 mg of hymecromone and 100 mg of chenodeoxycholic acid.

15 kg of hymecromone are mixed with 5 kg of chenodeoxycholic acid and 2.25 kg of wheat starch. The mixture is wetted with an aqueous gelatine solution (gelatine 0.25 kg) and then transformed into granules by passing through a screen. After drying, 1.25 kg of algic acid, 1. kg of talcum and 0.25 kg of magnesium stearate are added. The calibrated mixture is compressed to a unit weight of 500 mg.

EXAMPLE 2

Tablet according to Example 1, covered with a sugar coating so as to obtain a coated tablet, using the conventional method.

EXAMPLE 3

Tablet according to Example 1, covered with a polymer-based film: cellulose derivatives, acrylic acid derivatives, for example.

EXAMPLE 4

Tablet containing 500 mg of hymecromone and 125 mg of chenodeoxycholic acid.

15 kg of hymecromone are mixed with 3.75 kg of chenodeoxycholic acid and 3.5 kg of wheat starch. The mixture is wetted with an aqueous gelatine solution (gelatine 0.25 kg) and then transformed into granules by passing through a screen. After drying, 1.25 kg of algic acid, 1 kg of talcum and 3.25 kg of magnesium stearate are added. The calibrated mixture is compressed to a unit weight of 500 mg.

EXAMPLE 5

Hard gelatine capsule containing 300 mg of hymecromone and 25 mg of chenodeoxycholic acid.

15 kg of hymecromone are mixed with 1.25 kg of chenodeoxycholic acid and 0.1 kg of magnesium stearate. The powder obtained is distributed in capsules at the rate of 327 mg per capsule.

EXAMPLE 6

Hard gelatine capsule containing 500 mg of hymecromone and 30 mg of chenodeoxycholic acid.

15 kg of hymecromone are mixed with 0.9 kg of chenodeoxycholic acid and 0.45 kg of magnesium stearate, The powder obtained is distributed in capsules at the rate of 327 mg per capsule.

EXAMPLE 7

Soft gelatine capsule containing 300 mg of hymecromone and 25 mg of chenodeoxycholic acid.

15 kg of hymecromone and 1.25 kg of chenodeoxycholic acid are dispersed in 20 kg of polyoxyethylene glycol 400. The suspension obtained is distributed in capsules at the rate of 725 mg per capsule.

EXAMPLE 8

Soft gelatine capsule containing 500 mg of hymecromone and 30 mg of chenodeoxycholic acid.

15 kg of hymecromone and 0.9 kg of chenodeoxycholic acid are dispersed in 20.35 kg of polyoxyethylene glycol 400. The suspension obtained is distributed in capsules at the rate of 725 mg per capsule.

EXAMPLE 9

Drinkable suspension containing 200 mg of hymecromone and 200 mg of chenodeoxycholic acid in 10 ml.

2 kg of hymecromone and 2 kg of chenodeoxycholic acid are ground in liquid medium (10 liters of purified water containing in solution 0.2 kg of non-ionic, surface-active Emulsov O extra P).

3 kg of Veegum K (colloidal natural silicate of magnesium and aluminum) are caused to swell in 40 liters of purified water, previously brought to 80° and containing 0.2 kg of sorbic acid as preservative.

40 kg of sugar are dissolved in the gel as obtained and then the crushed powder of the active principles is added. The suspension thus obtained is brought to the volume of 100 liters by adding purified water. The suspension can be colored (tartrazine yellow, for example) and aromatized (orange and lemon aromas, for example).

We claim:

1. New medicament, which can be used in the treatment of biliary lithiasis, wherein the active principle is the association of hymecromone (4-methyl-7-hydroxycoumarine) and chenodeoxycholic acid.

2. Medicament according to claim 1, characterised in that the content of hymecromone is between 100 and 500 mg per dose and that of chenodeoxycholic acid is between 20 and 300 mg per dose.

3. Medicament according to claim 1 or 2, presented in a pharmaceutical form adapted for oral administration, such as tablets, coated tablets, hard gelatine capsules, soft gelatine capsules, solutions, suspensions.

4. Medicament according to claim 3, in tablet form, comprising the association of the active principle and an excipient formed of gelatine, algic acid, talcum and magnesium stearate.

5. Medicament according to claim 4, in the form of a coated tablet, wherein the tablet is covered with a sugar coating.

6. Medicament according to claim 3, in the form of a covered tablet, wherein the tablet is covered with a polymer-based film.

7. Medicament according to claim 3, in the form of a hard gelatine capsule, wherein the powder of the association of the active principle and the excipient, such as magnesium stearate, are distributed in the capsule.

8. Medicament according to claim 3, in the form of a soft gelatine capsule, wherein the suspension of the active principle in polyoxyethylene glycol is in the capsule.

9. Medicament according to claim 3, in the form of a suspension, wherein the active principle is in suspension in purified aqueous medium containing a preservative.

* * * * *